United States Patent
Merizzi

(12) 
(10) Patent No.: US 6,756,065 B1
(45) Date of Patent: Jun. 29, 2004

(54) ANTI-OXIDANT PREPARATION BASED ON PLANT EXTRACTS FOR THE TREATMENT OF CIRCULATION AND ADIPOSITY PROBLEMS

(75) Inventor: Gianfranco Merizzi, Torino (IT)

(73) Assignees: Ceteris Holding B.V., Lugano (CH); Amsterdam (Olanda) Succursale Di Lugano ( * ) Notice: Subject to any disclaimer, the term of this patent is extended or adjusted under 35 U.S.C. 154(b) by 0 days.

(21) Appl. No.: 10/070,655

(22) PCT Filed: Sep. 8, 2000

(86) PCT No.: PCT/EP00/08875

§ 371 (c)(1),
(2), (4) Date: Jun. 4, 2002

(87) PCT Pub. No.: WO01/19158

PCT Pub. Date: Mar. 22, 2001

(30) Foreign Application Priority Data

Sep. 10, 1999  (CH) ............................................. 1663/99

(51) Int. Cl.$^7$ .............................................. A61K 35/78
(52) U.S. Cl. ........................ 424/752; 424/725; 424/766
(58) Field of Search ................................ 424/725, 752, 424/766, 773, 774, 775

(56) References Cited

U.S. PATENT DOCUMENTS 4,753,929 A * 6/1988 Matsumoto et al. .......... 514/27

5,523,090 A * 6/1996 Znaiden et al. ............. 424/401

FOREIGN PATENT DOCUMENTS

| GB | 2174904 | 11/1986 |
|---|---|---|
| WO | WO0119381 | 3/2001 |

OTHER PUBLICATIONS

Harborne et al. Phytochemical Dictionary; 1999, 2nd Ed. p. 396 and 930.*

Redox Report, vol. 5, Nos. 2–3, 2000, pp. 144–145; *Body Contouring Using An Oral Herbal Antioxidant Formulation—Centelaplus: A Dose Controlled Observational Study*, Wayne Reilly and Vivienne Reeve (XP–000990069).

* cited by examiner

Primary Examiner—Christopher R. Tate
Assistant Examiner—Patricia Patten
(74) Attorney, Agent, or Firm—Roylance, Abrams, Berdo & Goodman, LLP

(57) ABSTRACT

A preparation based on plant extracts, with an antioxidant action which is particularly useful in the treatment of circulation and chronic degenerative problems and in the treatment of hypertension, characterized in that its active ingredients comprise *Ginkgo biloba* biflavones, catechin and/or epicatechin, cumarin and derivatives thereof and a component selected from among madecassic acid, asiatic acid, asiaticoside or combinations thereof.

18 Claims, No Drawings

ANTI-OXIDANT PREPARATION BASED ON PLANT EXTRACTS FOR THE TREATMENT OF CIRCULATION AND ADIPOSITY PROBLEMS

This Application is a 371 of PCT/EP00/08876 filed Sep. 8, 2000 which claims foreign priority to Application number 1663/99 filed in Switzerland on Sep. 10, 1999.

The present invention relates to a preparation based on plant extracts which has an antioxidant effect and is particularly useful in the prevention and treatment of circulation and chronic-degenerative problems, and in the prevention and treatment of hypertension.

This object is achieved according to the invention by providing a preparation characterised in that its active ingredients include a combination of *Ginkgo biloba* biflavones, catechin and/or epicatechin, cumarin and derivatives thereof, and an ingredient chosen from asiaticoside, asiatic acid, madecassic acid and compounds thereof.

This object is achieved according to the invention by providing a preparation characterised in that its active ingredients include a combination of *Ginkgo biloba* biflavones, catechine and/or epicatechine, cumarine and derivatives thereof, and an ingredient chosen from asiaticoside, asiatic acid, madecassic acid and compounds thereof.

The preparation is obtained by mixing plant extracts which contain the above active principles.

It is known that extracts from the leaves of *Ginkgo biloba* contain important active principles and in particular flavonol glucosides, lactonic terpenes and dimeric biflavones or flavones. The flavonol glucosides and the lactonic terpenes constitute the active components of standardized *Ginkgo biloba* extracts currently available on the market and are, respectively, powerful antibxidants and stimulants of nitric oxide and of effective platelet aggregating factor (PAF) antagonists. Thanks to the combined action of the active principles they contain, standard *Ginkgo biloba* extracts have proved to have a powerful vaso-motor effect, able to improve both central and peripheral blood flow. However, these extracts do not contain the biflavone component which is not extracted during normal processing. The *Ginkgo biloba* extract used in preparations according to the present invention is highly enriched with the biflavone component and, as a possible option, with extracts containing flavonol glucosides and lactonic terpenes. Five biflavones in particular have been identified in the biflavone component of *Ginkgo biloba*: these are, in particular, amentoflavone, bilobetine, isoginkgetine, ginkgetine and sciadopisitine; the five said compounds differ only by the presence of methyl compounds in some positions and, like all flavones, are powerful antioxidants. However, from a pharmacological point of view, they are characterised by their anti-phosphodiesterase, anti-inflammatory, vasculokinetic and anti-allergy properties. Phosphodiesterases (PDE) are cell enzymes responsible for interacting with cyclic nucleotides so as to linearize them. Cyclic nucleotides are involved as second messengers in transmitting intercellular signals and are thus responsible for some phenomena which are very important from a biochemical point of view. They assist with the visual process and in the relaxation of smooth muscles, they stimulate lipolysis in adiposity and vasculo-motion in capillary arterioles. More specifically, it is sufficient to report that in inhibiting PDE depending on cyclic AMP, these biflavones demonstrate an IC50 of 1.2 micromoles.

The anti-inflammatory properties of biflavones, and in particular those of amenthoflavone, have been demonstrated both in vitro, by measuring the interaction of these biflavones with cyclo-oxygenase, lipo-oxygenase e phospholipase A2, and in vivo, using various models of inflammation in animals (carragineen oedema, Croton oil inflammation etc). The anti-inflammatory action of biflavones was confirmed both in models using local application and in those in which they were administered intraperitoneally. In these models, the biflavones always demonstrated an anti-inflammatory action equivalent to that of indomethacyn or prednisolone. This effectiveness can be explained by analizing the IC50 of cyclo-oxygenase inhibition, which is 3 micromoles for amentoflavone.

With regard to the microvascularkinetic activity of biflavones, it should be reported that, following acute treatment, these substances improve the size of the arterial sphygma wave and, following chronic treatment they improve capillary density in tissues with trophic-connective problems, such as those affected by panniculopathy and/or various degrees of sclerodermy. Biflavones also have clear anti-allergy properties; they inhibit the release of histamine by mast-cells stimulated by allergens: thereby reducing or countering the formation of oedemas resulting from vasodilation and increases in vascular permeability.

In the context of the invention it is convenient to use an extract of leucocyanidine or leucoanthocyanin derived from *Vitis vinifera* as the source of catechin or epicatechin. Leucoanthocyanins are procyanidolic oligomers derived from condensing monomeric units of flavan-3-ols and flavan-3,4-diols, these being either free or esterified with gallic acid; leucoanthocyanines are powerful antioxidants. They are able to protect the endothelial wall of vessels and the extra-cellular matrix surrounding capillary wail's, as well as having anti-atherosclerotic properties owing to their antioxidant action on low-density lipoproteins (LDL) in blood.

The extracts are preferably used in a phytosomal form, in which the active components are complexed with phospholipids.

In the context of the invention, it is convenient to use an extract of leucocyanidine or leucoanthocyanin derived from *Vitis vinifera* as the source of catechin or epicatechin. Leucoanthocyanins are procyanidolic oligomers derived from condensing monomeric units of flavan-3-ols and flavan-3,4-diols, these being either free or esterified with gallic acid; leucoanthocyanines are powerful antioxidants. They are able to protect the endothelial wall of vessels and the extra-cellular matrix surrounding capillary walls, as well as having anti-atherosclerotic properties owing to their anti-oxidant action on low-density lipoproteins (LDL) in blood.

These active principles have a good bio-availability even when administered orally and their tropism have been demonstrated for the cardiovascular system and for all tissues, such as artery walls, which are rich in glycoamminoglycene.

Preferably, phytosomal forms of extracts are used, thus further enhancing the bioavailability of the active principles. In this form the procyanidines are complexed with phospholipids, particularly with soya distearoylphosphatidyecholine.

The preferable source of cumarin cumarine is an extract of *Meliotus officinea*, cumarin and its derivatives being the main active principles thereof; the main active principles of this extract are melilotine (3,4 dihydro-cumarine), melilotic acid (hydroxycumarinic acid), meliloltoside (melilotin glucoside) and some flavonoids which act like vitamin P; the active ingredients contained in the extract are particularly effective in increasing capillary strength, in reducing vascular permeability, in stimulating venous circulation and improving lymphatic circulation.

Extract of Melilotus may be replaced or backed up, as a source of cumarine and its derivatives, by an extract of Aesculus hippocastanum (horse chestnut) in the same dosage or up to around twice the dose of Melilotus extract.

The most abundant active ingredient of *Aesculus hippocastanum* extract, obtained from the bark, the pericarp of the fruit, the leaves or the buds, is cumarine glucoside, esculoside (6-0-glucosil-7-hydroxy-cumarine).

Other cumarins ctziari ies acontained in the extract are fraxine (8-0-glycoside-7-hydroxy-6-mehoxycumarin) and aglicone, esculetine (6,7-dioxy-cumarin) and fraxetine (7,8-dioxy-6-methoxy-cumarin).

The preferred source of asiaticoside, asiatic acid and madecassic acid is an extract containing a triterpene fraction of centella (*Centella asiatica*) which contains a combination of the above three active principles. The extract should preferably be used in a phytosomal form, obtained by a reaction between the triterpene fraction of the *Centella asiatica* with a phospholipid. A main action of the triterpene fraction of centella consists in accelerating the uptake and metabolism of lysine and of proline, thus increasing the synthesis and the release of tropocollagen and stimulating the turnover of acid mucopolysaccharides in connective tissue.

The basic composition of the invention can thus be obtained by mixing a *Ginkgo biloba* biflavone extract (perhaps in combination with a standard *Ginkgo biloba* extract also containing flavonol glucosides and lactonic terpenes), leucocyanidine extract, *Melilotus officinalis* extract and Centella extract; these extracts preferably being in a phytosomal form except for the *Melilotus officinalis* extract.

With reference to the extracts normally available on the market, the basic composition is preferably made up by the following percentages by weight:

2.5–40% *Ginkgo biloba* biflavone extract;
15–80% of leucocyanidine extract;
2.5–60%, preferably 2.5–30% of *Melilotus officinalis* and/or *Aesculus hippocastanum* extract;
2.5–40% of centella extract; possibly in combination with:
2.5–40% of standard *Ginkgo biloba* extract containing flavonol glucosides and lactonic terpenes. In terms of the content of active principles, the composition of the invention preferably contains the following percentages by weight:

0.2–14%, preferably 0.8–5% of total biflavones, expressed as ginkgetine content,
0.5–16%, preferably 1.5–6% of catechin and/or epicatechin, expressed as catechin content;
0.1–6%, preferably 0.4–2% of cumarin and its derivatives;
0.3–18%, preferably 0.9–6% of asiaticoside;
0.4–26%, preferably 1.4–9 % of asiatic acid and/or madecassic acid;
and possibly one or more of the following substances:
0.2–10%, preferably 0.6–4%, of flavonol glucosides and up to 1.3–2%, preferably up to 0.5%, of ginkgolide lactonic terpenes (bilobalide).

The composition can also contain active ingredients chosen from gamma-linolenic acid, eicosapentaenoic acid (EPA), docohexaenoic acid (DHA), ruscogenin and/or neoruscogenin, flavinoids such as vitexine, hyoside, proanthocyanidine, epicatechin and crategolic acid and mixtures thereof.

Gamma-linolenic acid is preferably introduced into the preparation in borage oil, added in quantities of 50 to 180% by weight with reference to 100 parts of basic mixture.

The preferred source of eicosapentaenoic acid (EPA) and of docohexaenoic acid (DHA) is fish oil which, with reference to 100 parts of the basic composition, may be added in quantities of 25 to 120% by weight.

The preferred source of ruscogenin and/or neoruscogenin is an extract of *Ruscus aculeatus* (Butcher's broom), this extract is preferably added in quantities of 5 to 50% by weight, with reference to 100 parts of the basic mixture.

The preferred source of flavonoids is an oily maceration of hawthorn *Crataegus oxyacantha* which, with reference to 100 parts of the basic mixture, can be added in quantities from 25 to 100% by weight.

In particular, in the preferred embodiment of the invention, the composition includes one or more of the following components in the following percentage amounts referred to the total composition:

3–36%, preferably 10–12% of gamma-linolenic acid;
2–36%, prererably 7–12% of eicosapentaenoic acid;
1.5–24%, preferably 5–8 % of docohexaenoic acid;
0.1–6%, preferably 0.4–2% of ruscogenin and/or neoruscogenin; and
up to 0.4%, preferably up 0.2% of flavonoids, expressed as a quantity of hyoside.

For example, a typical composition could be formulated according to the data in the table below, which gives the preferred minimum and maximum quantities by weight of the components of the basic mixture (marked with an asterisk) and of optional ingredients.

|  | Minimum (Parts by weight) | Maximum (Parts by weight) |
| --- | --- | --- |
| *Dry extract of *Vitis vinifera* (optionally phytosomes) | 20 | 200 |
| Oily maceration of hawthorn | 20 | 100 |
| *Dry extract of *Centella asiatica* (optionally phytosomes) | 20 | 100 |
| *Dry extract of *Melilotus officinalis* and/or *Aesculus hippocastanum* | 5 | 40 |
| Dry extract of *Ruscus aculeatus* | 5 | 100 |
| Dry extract of *Ginkgo biloba* (optionally phytosomes) | 10 | 75 |
| *Dimeric flavones of *Ginkgo biloba* (optionally phytosomes) | 10 | 75 |
| Borage oil | 50 | 1000 |
| Fish oil | 50 | 750 |
| Soya lecithin | 20 | 1000 |

Dosage 1–3 capsules per day.

In the above table, the given values, expressed in parts by weight, correspond, when expressed in milligrams to the minimum and maximum recommended daily doses or to the dose per capsule.

The preparation of the invention is formulated in forms suited to be taken orally, such as, for example, gelatin capsules with either soft or hard cases, tablets, pills, elixirs, suspensions and syrups. The mix of extracts can be administered orally, possibly in an edible vehicle or can be incorporated directly into food as part of a diet.

The composition is particularly useful in the prevention and treatment of circulation and chronic degenerative problems caused by damage to the vascular endothelium, the extracellular matrix or to surrounding tissues of the arterial, venous or lymphatic systems.

In the arterial system, such damage can be translated, for example, into reactions causing the formation of atherotomes leading to atherosclerosis, to the onset of ischemic processes due to the a narrowing of the arteries and to the onset of thrombotic problems caused by an atherome possibly becoming detached. In the venous system, dilation and loss of permeability of the vessels can, for example, cause chronic venous insufficiency and the onset of venous thrombotic troubles. In addition, some problems affecting the venous system can be a result of damage to lymphatic vessels, which, among other things, are responsible for draining tissues and circulating lymph.

The compositon of the invention provides an association of substances which are well understood from both a pharmacological and a clinical point of view, which is totally free of side effects and is particularly well suited to the treatment and the prevention of the main problems affecting the circulation system, including the heart, and that of chronic degenerative problems linked thereto.

Clinical trials have also shown that the preparation is able to reduce both arterial and diastolic blood pressure and is thus particularly useful in the treatment and prevention of hypertension.

What is claimed is:

1. A pharmaceutically acceptable composition for treating blood circulation problems comprising as active ingredients:
   either 2.5–40 wt % *Ginkgo biloba* biflavone extract or 2.5–40 wt % of standardized *Giakgo bilboa* extract containing biflavone glucosides and lactonic terpenes,
   catechin and/or epicatechin,
   cumarin and/or derivatives thereof and
   a component chosen from madecassic acid, asiatic acid, asiaticoside or combinations thereof.

2. A composition according to claim 1, characterized in that said extracts are complexed with a phospholipid.

3. A composition according to claim 2 wherein said phospholipid is soya distearoylphosphatidyecholine.

4. A composition according to claim 1, further comprising an active ingredient chosen from a group consisting of gamma-linolenic acid, icosapentaenoic acid, docohexaenoic acid, ruscogenin and/or neoruscogenin, flavonoids and combinations thereof.

5. A composition according to claim 4, in which said flavonoids are selected from vitexine, hyoside, proanthocyanidine, epicatechin crategolic acid and combinations thereof.

6. A composition according to claim 1 characterized in that said composition comprises:
   15–80% of leucocyanidine extract;
   2.5–30% of Melilotus and/or Aesculus hyppocastanum extract;
   2.5–40% of centella extract.

7. A composition according to claim 6, characterized in that with reference to 100 parts by weight of the basic mixture of claim 7, said composition also includes one or more of the following components:
   from 50 to 180% by weight of borage oil;
   from 25 to 120% by weight of fish oil;
   from 5 to 50% by weight of Ruscus aculeatus (Butcher's broom) extract; and
   from 25 to 100 % by weight of a maceration of Crataegus oxyacantha (hawthorn).

8. A coinposition according to claim 6 further comprising:
   2.5–40% of standardized *Ginkgo biloba* extract containing flavone glucosides and lactonic terpenes.

9. A composition according to claim 1 wherein said composition includes:
   0.2–14% by weight of total biflavones;
   0.5–16% by weight of catechin and/or epicatechin;
   0.1–6% by weight of cumarin and derivatives thereof;
   0.3–18% by weight of asiaticoside;
   0.4–26% by weight of asiatic acid and/or madecassic acid.

10. A composition according to claim 9, characterized in that said composition further comprises one or more of the following components:
    3–36% wt of gamma-linolenic acid;
    2–36% wt of eicosapentanoic acid;
    1.5 to 24% wt of docohexaenoic acid;
    0.1–6% wt of ruscogenin and/or neoruscogenin; and
    up to 0.4% wt of flavonoids.

11. A composition according to claim 10, further comprising one or more of the following components:
    10–12% of gamma-linolenic acid;
    17–12% of eicosapentanoic acid;
    5–8% of docohexaenoic acid;
    4–2% of ruscogenin and/or neoruscogenin; and
    up to 0.2% of flavonoids.

12. A composition according to claim 9 which includes:
    0.8–5% by weight of total biflacones;
    1.5–6% by weight of catechin and/or epicatechin;
    0.4–2% by weight of cumarin and derivatives thereof;
    0.9–6% by weight of asiaticoside;
    1.4–9% by weight of asiatic acid and/or madecassic acid.

13. Acomposition according to claim 12 comprising:
    0.2–10% of flavonol glucosides and
    up to 1.3% of lactonic terpenes.

14. A composition according to claim 13 comprising:
    0.6–4% by weight of flavonol glucosides and
    up to 0.5% by weight of lactonic terpenes.

15. A composition according to claim 1 wherein said composition is in a pharmaceutical form suitable for oral administration.

16. A method for treating circulation comprising the oral administration of a composition according to claim 1 to a patient afflicted with circulation problems.

17. A method according to claim 16 wherein said composition is administered at a rate and time sufficient to improve arterial sphygma wave size in said patient.

18. A method according to claim 16 wherein said composition is administered at a rate and for a time sufficient to improve capillary density in said patient.

* * * * *